(12) United States Patent
Ma et al.

(10) Patent No.: US 12,054,757 B1
(45) Date of Patent: Aug. 6, 2024

(54) PfAgo MUTANT PROTEIN MESOPHILIC TARGET NUCLEIC ACID CLEAVAGE ACTIVITY AND APPLICATION THEREOF

(71) Applicant: Hubei University, Wuhan (CN)

(72) Inventors: Lixin Ma, Wuhan (CN); Longyu Wang, Wuhan (CN); Fei Wang, Wuhan (CN); Xiaochen Xie, Wuhan (CN); Wanping Chen, Wuhan (CN); Fuyong Huang, Wuhan (CN)

(73) Assignee: HUBEI UNIVERSITY, Wuhan (CN)

( * ) Notice: Subject to any disclaimer, the term of this patent is extended or adjusted under 35 U.S.C. 154(b) by 0 days.

(21) Appl. No.: 18/424,759

(22) Filed: Jan. 27, 2024

Related U.S. Application Data

(63) Continuation of application No. PCT/CN2023/104637, filed on Jun. 30, 2023.

(30) Foreign Application Priority Data

May 16, 2023  (CN) .......................... 202310562239.7

(51) Int. Cl.
| | |
|---|---|
| *C12N 9/22* | (2006.01) |
| *C12N 15/11* | (2006.01) |
| *C12N 15/90* | (2006.01) |
| *C12Q 1/6823* | (2018.01) |

(52) U.S. Cl.
CPC ................ *C12N 9/22* (2013.01); *C12N 15/11* (2013.01); *C12N 15/90* (2013.01); *C12Q 1/6823* (2013.01); *C12Y 301/00* (2013.01); *C12N 2310/20* (2017.05); *C12N 2800/80* (2013.01)

(58) Field of Classification Search
CPC ....................................................... C12N 9/22
See application file for complete search history.

(56) References Cited

FOREIGN PATENT DOCUMENTS

| | | | |
|---|---|---|---|
| CN | 114561374 A | | 5/2022 |
| CN | 115975985 A | | 4/2023 |

OTHER PUBLICATIONS

ISA (CNIPA), Written Opinion for PCT/CN2023/104637, Dec. 21, 2023.
Hubei University (Applicant), Claims of PCT/CN2023/104637, Jun. 30, 2023.

*Primary Examiner* — Tekchand Saidha
(74) *Attorney, Agent, or Firm* — Zhigang Ma (57) ABSTRACT

A *Pyrococcus furiosus* Argonaute (PfAgo) mutant protein with mesophilic target nucleic acid cleavage activity and an application thereof are provided. The PfAgo mutant protein has an amino acid mutation on at least one of a $617^{th}$ position and a $618^{th}$ position relative to the sequence shown in SEQ ID NO: 1, specifically, K617E/G and/or L618Y/F/W/G. Compared with a wild-type PfAgo protein, the provided PfAgo mutant protein has activity in the temperature range of 30-95 Celsius degree (° C.), effectively expanding application range of prokaryotic Argonaute (pAgo) protein.

13 Claims, 6 Drawing Sheets

Specification includes a Sequence Listing.

SEQUENCE LISTING

```
Sequence total quantity: 25
SEQ ID NO: 1              moltype = AA   length = 770
FEATURE                   Location/Qualifiers
source                    1..770
                          mol_type = protein
                          organism = Pyrococcus furiosus
SEQUENCE: 1
MKAKVVINLV KINKKIIPDK IYVYRLFNDP EEELQKEGYS IYRLAYENVG IVIDPENLII   60
ATTKELEYEG EFIPEGEISF SELRNDYQSK LVLRLLKENG IGEYELSKLL RKFRKPKTFG  120
DYKVIPSVEM SVIKHDEDFY LVIHIIHQIQ SMKTLWELVN KDPKELEEFL MTHKENLMLK  180
DIASPLKTVY KPCFEEYTKK PKLDHNQEIV KYWYNYHIER YWNTPEAKLE FYRKFGQVDL  240
KQPAILAKFA SKIKKNKNYK IYLLPQLVVP TYNAEQLESD VAKEILEYTK LMPEERKELL  300
ENILAEVDSD IIDKSLSEIE VEKIAQELEN KIRVRDDKGN SVPISQLNVQ KSQLLLWTNY  360
SRKYPVILPY EVPEKFRKIR EIPMFIILDS GLLADIQNFA TNEFRELVKS MYYSLAKKYN  420
SLAKKARSTN EIGLPFLDFR GKEKVITEDL NSDKGIIEVV EQVSSFMKGK ELGLAFIAAR  480
NKLSSEKFEE IKRRLFNLNV ISQVVNEDTL KNKRDKYDRN RLDLFVRHNL LFQVLSKLGV  540
KYYVLDYRFN YDYIIGIDVA PMKRSEGYIG GSAVMFDSQG YIRKIVPIKI GEQRGESVDM  600
NEFFKEMVDK FKEFNIKLDN KKILLLRDGR ITNNEEEGLK YISEMFDIEV VTMDVIKNHP  660
VRAFANMKMY FNLGGAIYLI PHKLKQAKGT PIPIKLAKKR IIKNGKVEKQ SITRQDVLDI  720
FILTRLNYGS ISADMRLPAP VHYAHKFANA IRNEWKIKEE FLAEGFLYFV             770

SEQ ID NO: 2              moltype = AA   length = 770
FEATURE                   Location/Qualifiers
source                    1..770
                          mol_type = protein
                          organism = synthetic construct
SEQUENCE: 2
MKAKVVINLV KINKKIIPDK IYVYRLFNDP EEELQKEGYS IYRLAYENVG IVIDPENLII   60
ATTKELEYEG EFIPEGEISF SELRNDYQSK LVLRLLKENG IGEYELSKLL RKFRKPKTFG  120
DYKVIPSVEM SVIKHDEDFY LVIHIIHQIQ SMKTLWELVN KDPKELEEFL MTHKENLMLK  180
DIASPLKTVY KPCFEEYTKK PKLDHNQEIV KYWYNYHIER YWNTPEAKLE FYRKFGQVDL  240
KQPAILAKFA SKIKKNKNYK IYLLPQLVVP TYNAEQLESD VAKEILEYTK LMPEERKELL  300
ENILAEVDSD IIDKSLSEIE VEKIAQELEN KIRVRDDKGN SVPISQLNVQ KSQLLLWTNY  360
SRKYPVILPY EVPEKFRKIR EIPMFIILDS GLLADIQNFA TNEFRELVKS MYYSLAKKYN  420
SLAKKARSTN EIGLPFLDFR GKEKVITEDL NSDKGIIEVV EQVSSFMKGK ELGLAFIAAR  480
NKLSSEKFEE IKRRLFNLNV ISQVVNEDTL KNKRDKYDRN RLDLFVRHNL LFQVLSKLGV  540
KYYVLDYRFN YDYIIGIDVA PMKRSEGYIG GSAVMFDSQG YIRKIVPIKI GEQRGESVDM  600
NEFFKEMVDK FKEFNIGGDN KKILLLRDGR ITNNEEEGLK YISEMFDIEV VTMDVIKNHP  660
VRAFANMKMY FNLGGAIYLI PHKLKQAKGT PIPIKLAKKR IIKNGKVEKQ SITRQDVLDI  720
FILTRLNYGS ISADMRLPAP VHYAHKFANA IRNEWKIKEE FLAEGFLYFV             770

SEQ ID NO: 3              moltype = DNA   length = 2313
FEATURE                   Location/Qualifiers
source                    1..2313
                          mol_type = other DNA
                          organism = synthetic construct
SEQUENCE: 3
atgaaagcca ttgtggtgat taacctggtg aaaatcaaca aaaaaatcat cccgggataaa   60
atctacgtgt accgcctgtt taatgatccg gaagaagaac tgcagaaaga aggctatagc  120
atttatcgtc tggcctatga aaatgtgggc attgttatcg atccggaaaa tctgattatt  180
gccaccacca agaactgga atatgaaggt gaatttattc cggaaggcga aatcagcttt  240
agcgaactgc gtaatgatta tcagagcaaa ctggttctgc gtctgctgaa agaaaatggt  300
attggtgaat atgaactgtc caaactgctg cgcaaatttc gtaaaccgaa aacctttggc  360
gattacaaag ttattccgag cgttgaaatg agcgtgatca acacgatga gatttctat  420
ctggtgatcc atatcatcca tcagatccag agcatgaaaa ccctgtggga actggttaat  480
aaagatccga aagagctgga agaatttctg atgacccata agaaaaacct gatgctgaaa  540
gatattgcca gtccgctgaa aaccgtgtat aaaccgtgtt ttgaagaata taccaaaaaa  600
ccgaaactgg accacaacca agagatcgtg aaatattggt ataactatca catcgagcgc  660
tattggaata caccggaagc aaaactggaa ttctatcgca aatttggtca ggtggatctg  720
aaacagcctg caattctggc aaaatttgca agcaaaatta aaaaaaataa aaactacaaa  780
atctatctgc tgccgcagct ggttgttccg acctataatg cagaacagct ggaaagtgat  840
gtggccaaag aaattctgga atatacaaaa ctgatgcctg aggaacgtaa agagctgctg  900
gaaaatattc tggcagaagt ggatagcgat atcatcgata aagcctgag cgaaatcgag  960
gttgaaaaaa ttgcacaaga actggaaaac aaaatccgcg tgcgtgatga taagggtaat 1020
agcgttccga ttagccagct gaatgttcag aaaagcctgc tgctgctgtg gaccaattat 1080
tcacgtaaat atccggttat cctgccgtat gaagtgccgg aaaaatttcg caaattcgt 1140
gaaatcccga tgttcattat tctggatagc ggtctgctgg cagatattca gaactttgca 1200
accaatgaat ttcgcgagct ggtcaaaagc atgtattata gcctggccaa aaaatacaac 1260
tccctggcaa aaaagcacg cagcaccaat gaaattggtc tgccgtttct ggattttcgc 1320
ggtaaagaaa aagtgatcac cgaagatctg aatagcaaag gcattattga agttgtt 1380
gaacaggtga gcagctttat gaaaggtaaa gaactgggtc tggcatttat tgcagcacgt 1440
aataaactga gcagcgagaa atttgaagaa atcaaacgcc gtctgtttaa cctgaatgtt 1500
attagccagg tggtgaatga agataccctg aaaaacaaac gcgataaata tgatcgtaat 1560
cgcctggacc tgtttgttcg tcataatctg ctgttccagg ttctgagtaa actgggtgtt 1620
aaatactatg tgctggacta cgcttcaac tacgattata tcattggcat tgatgtggca 1680
ccgatgaaac gtagcgaagg ttatattggt ggtagcgcag ttatgtttga tagccagggt 1740
tatattcgta aaatcgtgcc gattaaaatc ggtgaacagc gtggtgaaag cgttgatatg 1800
aacgaatttt tcaaagaaat ggtggacaaa ttcaagagt tcaacatcgg gggggataac 1860
```

-continued

```
aaaaaaatcc tgctgctgcg tgatggtcgc attaccaata atgaagaaga aggcctgaaa 1920
tatatcagcg agatgttcga tattgaagtg gttaccatgg atgtgatcaa aaaccatccg 1980
gttcgtgcat ttgcaaacat gaaaatgtat tttaacctgg gtggtgccat ttatctgatt 2040
ccgcataaac tgaaacaggc aaaaggcacc ccgattccga ttaaactggc gaaaaaacgc 2100
attatcaaaa acggcaaagt ggaaaaacag agcattaccc gtcaggatgt tctggatatc 2160
tttattctga cccgtctgaa ttatggtagc attagcgcag atatgcgtct gcctgcaccg 2220
gttcattatg cacataaatt tgccaatgcc attcgcaacg agtggaaaat caaagaagaa 2280
ttcctggccg aaggctttct gtattttgtt taa                               2313

SEQ ID NO: 4            moltype = DNA  length = 45
FEATURE                 Location/Qualifiers
source                  1..45
                        mol_type = other DNA
                        organism = synthetic construct
SEQUENCE: 4
aaacgacggc cagtgccaag cttactatac aacctactac ctcat                  45

SEQ ID NO: 5            moltype = RNA  length = 45
FEATURE                 Location/Qualifiers
source                  1..45
                        mol_type = other RNA
                        organism = synthetic construct
SEQUENCE: 5
aaacgacggc cagtgccaag cttactatac aacctactac ctcat                  45

SEQ ID NO: 6            moltype = DNA  length = 18
FEATURE                 Location/Qualifiers
source                  1..18
                        mol_type = other DNA
                        organism = synthetic construct
SEQUENCE: 6
tgaggtagta ggttgtat                                                18

SEQ ID NO: 7            moltype = RNA  length = 18
FEATURE                 Location/Qualifiers
source                  1..18
                        mol_type = other RNA
                        organism = synthetic construct
SEQUENCE: 7
tgaggtagta ggttgtat                                                18

SEQ ID NO: 8            moltype = DNA  length = 30
FEATURE                 Location/Qualifiers
source                  1..30
                        mol_type = other DNA
                        organism = synthetic construct
SEQUENCE: 8
tgaggtagta ggttgtatag taagcttggc                                   30

SEQ ID NO: 9            moltype = RNA  length = 30
FEATURE                 Location/Qualifiers
source                  1..30
                        mol_type = other RNA
                        organism = synthetic construct
SEQUENCE: 9
tgaggtagta ggttgtatag taagcttggc                                   30

SEQ ID NO: 10           moltype = DNA  length = 45
FEATURE                 Location/Qualifiers
source                  1..45
                        mol_type = other DNA
                        organism = synthetic construct
SEQUENCE: 10
aaacgacggc cagtgccaag cttactatac aacctactac ctctt                  45

SEQ ID NO: 11           moltype = DNA  length = 45
FEATURE                 Location/Qualifiers
source                  1..45
                        mol_type = other DNA
                        organism = synthetic construct
SEQUENCE: 11
aaacgacggc cagtgccaag cttactatac aacctactac ctcct                  45

SEQ ID NO: 12           moltype = DNA  length = 45
FEATURE                 Location/Qualifiers
source                  1..45
                        mol_type = other DNA
                        organism = synthetic construct
SEQUENCE: 12
```

-continued

```
aaacgacggc cagtgccaag cttactatac aacctactac ctcgt          45

SEQ ID NO: 13              moltype = RNA   length = 45
FEATURE                    Location/Qualifiers
source                     1..45
                           mol_type = other RNA
                           organism = synthetic construct
SEQUENCE: 13
aaacgacggc cagtgccaag cttactatac aacctactac ctctt          45

SEQ ID NO: 14              moltype = RNA   length = 45
FEATURE                    Location/Qualifiers
source                     1..45
                           mol_type = other RNA
                           organism = synthetic construct
SEQUENCE: 14
aaacgacggc cagtgccaag cttactatac aacctactac ctcct          45

SEQ ID NO: 15              moltype = RNA   length = 45
FEATURE                    Location/Qualifiers
source                     1..45
                           mol_type = other RNA
                           organism = synthetic construct
SEQUENCE: 15
aaacgacggc cagtgccaag cttactatac aacctactac ctcgt          45

SEQ ID NO: 16              moltype = DNA   length = 18
FEATURE                    Location/Qualifiers
source                     1..18
                           mol_type = other DNA
                           organism = synthetic construct
SEQUENCE: 16
catgagcgga tacatatt                                        18

SEQ ID NO: 17              moltype = DNA   length = 18
FEATURE                    Location/Qualifiers
source                     1..18
                           mol_type = other DNA
                           organism = synthetic construct
SEQUENCE: 17
caaatatgta tccgctca                                        18

SEQ ID NO: 18              moltype = DNA   length = 18
FEATURE                    Location/Qualifiers
source                     1..18
                           mol_type = other DNA
                           organism = synthetic construct
SEQUENCE: 18
tcaaaaagga tcttcacc                                        18

SEQ ID NO: 19              moltype = DNA   length = 18
FEATURE                    Location/Qualifiers
source                     1..18
                           mol_type = other DNA
                           organism = synthetic construct
SEQUENCE: 19
taggtgaaga tccttttt                                        18

SEQ ID NO: 20              moltype = DNA   length = 18
FEATURE                    Location/Qualifiers
source                     1..18
                           mol_type = other DNA
                           organism = synthetic construct
SEQUENCE: 20
aagaaaccat tattatca                                        18

SEQ ID NO: 21              moltype = DNA   length = 18
FEATURE                    Location/Qualifiers
source                     1..18
                           mol_type = other DNA
                           organism = synthetic construct
SEQUENCE: 21
catgataata atggtttc                                        18

SEQ ID NO: 22              moltype = DNA   length = 18
FEATURE                    Location/Qualifiers
source                     1..18
                           mol_type = other DNA
                           organism = synthetic construct
```

```
SEQUENCE: 22
aaaagtgctc atcattgg                                                       18

SEQ ID NO: 23           moltype = DNA  length = 18
FEATURE                 Location/Qualifiers
source                  1..18
                        mol_type = other DNA
                        organism = synthetic construct
SEQUENCE: 23
ttccaatgat gagcactt                                                       18

SEQ ID NO: 24           moltype = DNA  length = 18
FEATURE                 Location/Qualifiers
source                  1..18
                        mol_type = other DNA
                        organism = synthetic construct
SEQUENCE: 24
cagggtttc ccagtcac                                                        18

SEQ ID NO: 25           moltype = DNA  length = 18
FEATURE                 Location/Qualifiers
source                  1..18
                        mol_type = other DNA
                        organism = synthetic construct
SEQUENCE: 25
tcgtgactgg gaaaaccc                                                       18
```

PfAgo MUTANT PROTEIN MESOPHILIC TARGET NUCLEIC ACID CLEAVAGE ACTIVITY AND APPLICATION THEREOF

TECHNICAL FIELD

The disclosure relates to the field of programmable nuclease technologies, and more particularly to a *Pyrococcus furiosus* Argonaute (PfAgo) mutant protein with mesophilic target nucleic acid cleavage activity and an application thereof.

STATEMENT REGARDING SEQUENCE LISTING

The sequence listing associated with this application is provided in text format in lieu of a paper copy and is hereby incorporated by reference into the specification. The name of the XML file containing the sequence listing is 23015JHG-USP1-SL.xml. The XML file is 26,917 bytes; is created on Jan. 14, 2024; and is being submitted electronically via Patent Center.

BACKGROUND

Argonaute (Ago) proteins are a novel class of programmable nucleases, which are widely distributed in eukaryotes, eubacteria, and archaebacteria. Most eukaryotic Ago (eAgo) proteins have been found to recognize a target RNA by using 5'-phosphorylated guide RNA (5'P-gRNA), which plays an important role in RNA interference pathway in eukaryotes. Most prokaryotic Ago (pAgo) proteins use 5'-phosphorylated guide DNA (5'P-gDNA) to recognize a target DNA. There is a lack of RNA interference pathway in prokaryotes. Although recent studies have shown that the pAgo proteins can defend against invasive genetic elements in the host and participate in various intracellular activities, the physiological function of the pAgo protein is not particularly clear at present. As a programmable nuclease, clustered regularly interspaced short palindromic repeats (CRISPR)-associated proteins have been reported to be applied in different fields. Similar to the CRISPR-associated proteins, the Ago protein, as a new programmable nuclease, has been reported to be applied to molecular cloning, molecular diagnosis, intracellular RNA and genome editing, in vivo imaging, and so on. Compared with CRISPR-associated (Cas) system, which needs a specific motif on the target and can only use RNA as the guide strand, the pAgo proteins exhibit precise endonuclease activity on any target sequence, and can use both RNA and DNA as guide nucleic acids, thus it has great potential in applications such as intracellular RNA and genome editing.

PfAgo is a pAgo protein derived from extremely thermophilic bacterium *Pyrococcus furiosus*. PfAgo can cleave target DNA under the guidance of 5'P-gDNA, and its activity is the highest in the temperature range of 87-99.99° C., while it cannot cleave the target DNA in a short time at 37° C. PfAgo has high DNA target cleavage activity mediated by 5'P-gDNA at high temperature, which makes it have been used in molecular cloning and molecular diagnosis. However, PfAgo has almost no activity at 37° C., which limits its application in intracellular RNA and genome editing. Moreover, enzymes with thermal stability and catalytic activity at low temperature are not only easy to store, but also have a wider range of applications.

Adaptation of organisms to environmental niches is a hallmark of evolution. One prevalent example is that of thermal adaptation, in which two descendants evolve at different temperature extremes. Underlying physiological differences between such organisms are changes in enzymes catalyzing essential reactions, with orthologues from each organism undergoing adaptive mutations that preserve similar catalytic rates at their respective physiological temperatures. However, sequence changes responsible for these adaptive differences are often at surface exposed sites distant from the substrate binding site, leaving the active site of the enzyme structurally unperturbed. How such changes are allosterically propagated to the active site, to modulate activity, is not known. In 2018, Harry G. Saavedra et al. proposed that dynamic allostery can drive cold adaptation in enzymes, and allosteric mutation sites were selected to increase the probability of local unfolding, while preserving the ground state structure (Harry G. Saavedra et al., "Dynamic allostery can drive cold adaptation in enzymes", Nature, 2018, pp. 324-328, Vol. 558, No. 7709.). In 2019, Satoshi Akanuma et al. showed an effective way to explore amino acid substitutions that enhance the low-temperature catalytic activity of a thermophilic enzyme, based on a pairwise sequence comparison of thermophilic/mesophilic enzymes (Satoshi Akanuma et al., "Establishment of mesophilic-like catalytic properties in a thermophilic enzyme without affecting its thermal stability", Scientific Reports, 2019, pp. 1-11, Vol. 9, No. 9346.).

SUMMARY

In view of the above, the disclosure aims to perform structure-based mutant screening of a *Pyrococcus furiosus* Argonaute (PfAgo) protein to discover PfAgo mutant proteins with good activity under the mesophilic condition. It not only paves the way for intracellular RNA targeting, gene editing and other applications, expands the application range of prokaryotic Argonaute (pAgo) protein, but also provides a strategy to modify thermophilic Ago proteins (also referred to as high-temperature Ago proteins).

Technical solutions of the disclosure are as follows.

In a first aspect, the purpose of the disclosure is to provide PfAgo mutant proteins with mesophilic target nucleic acid cleavage activity. Compared with wild-type PfAgo protein, these mutant proteins have mutations in amino acids within 8 angstroms (Å) to 20 Å away from an active site and a binding substrate, resulting in a change in catalytic activity temperature. The active site of the disclosure specifically refers to the DEDH catalytic tetramer of the wild-type PfAgo protein.

Specifically, a mutation site of the PfAgo mutant protein provided by the disclosure is at least one of a $617^{th}$ position and a $618^{th}$ position of the sequence shown in SEQ ID NO: 1 (amino acid sequence of the wild-type PfAgo protein). In the sequence shown in SEQ ID NO: 1, the amino acid at $617^{th}$ position is lysine (Lys, K) and the amino acid at $617^{th}$ position is leucine (Leu, L).

In the PfAgo mutant protein provided by the disclosure, the lysine at $617^{th}$ position is mutated into any amino acid other than lysine, and the leucine at $618^{th}$ position is mutated into any amino acid other than leucine.

Compared with the wild-type PfAgo protein, the PfAgo mutant protein provided by the disclosure has target cleavage activity at 30-95° C., thus expanding the application range of the PfAgo protein and making it have the potential to be applied to intracellular RNA and genome editing.

In an embodiment, in the PfAgo mutant protein provided by the disclosure, the lysine at the $617^{th}$ position is mutated into glutamic acid (Glu, E) or glycine (Gly, G), which is recorded as K617E/G. The leucine at the 618$^{th}$ position is mutated into tyrosine (Tyr, Y), phenylalanine (Phe, F), tryptophan (Trp, W), or glycine, which is recorded as L618Y/F/W/G.

It can be summarized as follows based on data of embodiments of the disclosure.
- (a1) When the lysine at the 617$^{th}$ position is mutated into the glutamic acid or the glycine, the two obtained mutant proteins can cleave target DNA under the guidance of guide DNA at 37° C., and the mutant protein obtained after the lysine at the 617$^{th}$ position is mutated into the glycine has better activity at 37° C.
- (a2) When the leucine at 618$^{th}$ position is mutated into tyrosine, phenylalanine, tryptophan, and glycine respectively, the four mutant proteins can cleave the target DNA under the guidance of the guide DNA at 37° C. Among them, the mutant protein obtained after the leucine at 618$^{th}$ position is mutated into the tyrosine or the glycine has better activity at 37° C., and can also cleave the target RNA under the guidance of the guide DNA. The mutant protein obtained after the leucine at 618$^{th}$ position is mutated into the glycine can also cleave the target RNA under the guidance of 5'-phosphorylated guide RNA (5'P-gRNA).
- (a3) When the positions 617$^{th}$ and 618$^{th}$ are mutated simultaneously, specifically into the glycine and the tyrosine (i.e., K617E and L618Y) respectively, or into glycine (i.e., K617G and L618G), the obtained two mutant proteins is further improved in activity at 37° C. and can cleave the target DNA and the target RNA under the guidance of the guide DNA. Among them, the mutant protein obtained by simultaneously mutating the positions 617$^{th}$ and 618$^{th}$ into glycine (i.e., PfAgo_K617G/L618G) has the optimal activity at 37° C., and can also cleave the target RNA under the guidance of 5'P-gRNA.

In a second aspect, the purpose of the disclosure is to provide several biomaterials related to the above PfAgo mutant protein, including:
- (b1) a nucleic acid molecule encoding the PfAgo mutant protein;
- (b2) an expression cassette or a vector containing the nucleic acid molecule described in (b1); and
- (b3) a transformant containing the vector described in (b2).

For the nucleic acid molecule described in (b1), an embodiment of the disclosure provides the nucleotide sequence of the nucleic acid molecule as shown in SEQ ID NO: 3, the nucleic acid molecule encodes the PfAgo mutant protein in which the lysine at 617$^{th}$ position and the leucine at 618$^{th}$ position are mutated into glycine simultaneously (i.e., PfAgo_K617G/L618G), and the amino acid sequence of the PfAgo mutant protein is shown in SEQ ID NO: 2.

For the vector described in (b2), it can be a pET plasmid, as an embodiment of the disclosure, the nucleic acid fragment encoding the PfAgo mutant protein is connected to pET-28a to obtain a recombinant vector.

For the transformant described in (b3), the transformant is obtained by transforming the recombinant vector into a host cell, which can be a conventional host cell in the field, but it must be able to satisfy the stable self-replication of the recombinant vector and the nucleic acid molecule encoding the PfAgo mutant protein can be effectively expressed.

Using the above biomaterials, the PfAgo mutant protein can be prepared.

In a third aspect, the purpose of the disclosure is to provide a nucleic acid cleavage system, including:
- (c1) a single-stranded guide nucleic acid; and
- (c2) the PfAgo mutant protein provided by the disclosure.

In the above nucleic acid cleavage system, the single-stranded guide nucleic acid is 5'P-gRNA, 5'P-gDNA, or 5'-hydroxylated guide DNA (5'OH-gDNA); and the length of the single-stranded guide nucleic acid is in a range of 12 to 30 nucleotides.

In an embodiment, the length of the single-stranded guide nucleic acid is in a range of 15 to 19 nucleotides. In a specific embodiment, the length of the single-stranded guide nucleic acid is 18 nucleotides.

In a fourth aspect, the purpose of the disclosure is to provide an application of the above-mentioned nucleic acid cleavage system in specifically cleaving target RNA or target DNA. Specifically, the nucleic acid cleavage system is constructed, and then the target RNA or the target DNA is added to the system. If the target RNA or the target DNA is complementary to the single-stranded guide nucleic acid sequence, the PfAgo mutant protein specifically cleaves the target RNA or the target DNA under the guidance of the single-stranded guide nucleic acid.

In the above application, the target RNA has no advanced structure; or has an advanced structure; or is double-stranded RNA; or is in vitro transcribed RNA; or viral genomic RNA; or is messenger RNA (mRNA); or other RNA in the cell. The target DNA is single-stranded DNA or double-stranded DNA.

In the above application, complementary pairing specifically refers to the following two situations:
- the target RNA or the target DNA has a nucleotide sequence that is completely complementary to the single-stranded guide nucleic acid sequence; and
- the target RNA or the target DNA has a nucleotide sequence with single or multiple base mismatches with the single-stranded guide nucleic acid sequence, where the number of mismatches may be 1, 2, 3, 4 or 5, and the mismatches are usually isolated or may be continuous.

In the above application, the nucleic acid cleavage system includes at least one divalent metal cation selected from the group consisting of manganese ion ($Mn^{2+}$), magnesium ion ($Mg^{2+}$), and cobalt ion ($CO^{2+}$).

In an embodiment, the divalent metal cations are $Mn^{2+}$ and $Mg^{2+}$. In a specific embodiment, the divalent metal cations are $Mn^{2+}$.

In an embodiment, in the nucleic acid cleavage system, a final concentration of the divalent metal cations is in a range of 1-10 millimoles per liter (mM). The data of the embodiments show that when the single-stranded nucleic acid is 5'P-gDNA and the target is DNA, the concentration of $Mg^{2+}$ is in a range of 3-10 mM and the concentration of $Mn^{2+}$ is in a range of 2-10 mM. When the single-stranded nucleic acid is 5'P-gDNA and the target is RNA, the concentration of $Mg^{2+}$ is in a range of 2-10 mM and the concentration of $Mn^{2+}$ is in a range of 1-5 mM. When the single-stranded nucleic acid is 5'P-gRNA and the target is RNA, the concentration of $Mn^{2+}$ is in a range of 3-10 mM.

In a fifth aspect, the purpose of the disclosure is to provide a detection kit. The detection kit includes the PfAgo mutant protein provided by the disclosure. It can also include a single-stranded guide nucleic acid with a specific sequence according to the detection purpose.

In a sixth aspect, the purpose of the disclosure is to provide an intracellular gene editing method, specifically adopting the PfAgo mutant protein provided by the disclosure.

Compared with the related art, the disclosure has the beneficial effects as follows.
(1) By mutating the amino acids of the wild-type PfAgo protein within 8 angstroms (Å) to 20 Å away from an active site and a binding substrate, the PfAgo mutant protein with good activity at medium and low temperature is successfully screened, which provides a strategy to modify thermophilic Ago proteins.
(2) The PfAgo mutant protein provided by the disclosure improves its cleavage activity at medium temperature, and at the same time retains its heat-resistant ability, which is beneficial to the preservation and transportation of enzymes.
(3) Compared with the wild-type PfAgo protein, which can only cleave the target DNA at high temperature, the optimal mutant protein PfAgo_K617G/L618G provided by the disclosure can cleave the target DNA and the target RNA using the guide DNA and cleave the target RNA using 5'P-gRNA at 37° C., thus expanding its used temperature range, types of guide nucleic acids and types of cutting targets.
(4) The PfAgo_K617G/L618G protein has the activity of specifically cleaving the target RNA and the target DNA. The disclosure also provides the nucleic acid expression vector containing the sequence encoding PfAgo_K617G/L618G protein, and a composition, a kit and a method for cleaving and editing target nucleic acid in a sequence-specific manner, so that the PfAgo_K617G/L618G protein can be used in many fields of biotechnology, such as nucleic acid detection, molecular cloning, RNA and genome editing, etc.
(5) The PfAgo_K617G/L618G protein can cleave the target DNA using the guide DNA at 37° C., which lays the foundation for genome editing in vivo. The PfAgo_K617G/L618G protein can cleave the target RNA using the guide DNA at 37° C., which lays the foundation for RNA targeting in vivo. The PfAgo_K617G/L618G protein can cleave the target RNA using 5'P-gRNA at 37° C., which lays the foundation for RNA targeting in vivo by co-expression of protein and guide nucleic acid.
(6) The PfAgo_K617G/L618G protein strictly depends on the complementary pairing of the guide and the target to exert its cleavage activity, and there is no nonspecific "trans-cleavage" activity of clustered regularly interspaced short palindromic repeats (CRISPR)-associated proteins, and the specificity is better. The PfAgo_K617G/L618G protein uses a variety of guide nucleic acids, which can be either DNA or RNA, generally with shorter length, lower synthesis cost of DNA than RNA, and more stable and not easy to degrade. The pAgo complex formed by the PfAgo_K617G/L618G protein and the guide nucleic acid does not depend on special motifs near the target site to recognize and bind the target, and thus the guide nucleic acid is convenient to design without considering the site restriction.

DETAILED DESCRIPTION OF EMBODIMENTS

Technical solutions of the disclosure will be described clearly and completely below in combination with embodiments and the accompanying drawings. Apparently, the described embodiments are only some of the embodiments of the disclosure, but not all of the embodiments.

Unless otherwise specified, embodiments are all in accordance with conventional experimental conditions or conditions recommended by the manufacturer's instructions. The reagents and materials used are commercially available unless otherwise specified.

Embodiment 1 Screening and Preparation of PfAgo Mutants (1) Screening of PfAgo Structure-Based Mutation Sites The structure of PfAgo (PDB ID: 1U04) and the structure of CbAgo ternary complex (PDB ID: 6QZK) are downloaded from the Protein Data Bank (PDB) website. Firstly, the structure of PfAgo and the structure of the CbAgo ternary complex are loaded into PyMOL software, and then the structure of PfAgo and the structure of the CbAgo ternary complex are compared. The mutation sites are selected based on the following three principles. First, the side chain of the mutation site should be highly exposed to the surface and there is no intramolecular contact. Second, the mutant side chain should be far away from the binding substrate and active site (i.e., >8 angstroms abbreviated as A). Third, amino acids within a distance of 20 Å from the binding substrate and the active site are selected.

The PfAgo gene fragment as shown in SEQ ID NO: 1 is amplified from the recombinant plasmid pET23a-PfAgo, and the plasmid PET28A-PFago is obtained by connecting to pET28a by conventional methods.

According to the screened mutation sites, PfAgo mutants are constructed, including: PfAgo_K617E that the lysine at the $617^{th}$ position is mutated into glutamic acid, PfAgo_K617G that the lysine at $617^{th}$ position is glycine, PfAgo_L618Y that the leucine at $618^{th}$ position is mutated into tyrosine, PfAgo_L618F that the leucine at $618^{th}$ position is mutated into phenylalanine, PfAgo_L618W that the leucine at $618^{th}$ position is mutated into tryptophan, and PfAgo_L618G that the leucine at $618^{th}$ position is mutated into glycine. In an embodiment, PfAgo is subjected to combined mutation, including: PfAgo_K617E/L618Y that the lysine at $617^{th}$ position and the leucine at $618^{th}$ position are simultaneously mutated into glutamic acid and tyrosine respectively, and PfAgo_K617G/L618G that the lysine at $617^{th}$ position and the leucine at $618^{th}$ position are simultaneously mutated into glycine, etc. Among the above mutants, the amino acid sequence and the nucleotide sequence of PfAgo_K617G/L618G are shown in SEQ ID NO: 2 and SEQ ID NO: 3 respectively.

Primers are designed for different loci, the plasmid pET28a-PfAgo is used as the template for polymerase chain reaction (PCR), and mutant plasmids are obtained by T5 recombinant cloning.

(2) Expression and Purification of PfAgo and its Mutants

PfAgo and its mutant plasmids are transformed into *Escherichia coli* BL21(DE3) respectively, and single colonies are selected and cultured in 5 milliliters (mL) Lysogeny broth (LB) liquid medium at 37° C. in a shaker overnight, and then transferred to a large bottle of Terrific broth (TB) medium containing 50 milligrams per milliliter (mg/mL) kanamycin according to the ratio of 5:1. When the value of optical density at 600 nanometers (OD600) is 0.6-0.8, isopropyl β-D-1-thiogalactopyranoside (IPTG) with a final concentration of 0.5 millimoles per liter (mM) is added, and the protein expression is induced at 18° C. in a shaker for 16-20 hours.

The bacteria are collected by a high-speed centrifuge at 6000 revolutions per minute (rpm) for 10 minutes, and the supernatant is removed. The collected bacteria were suspended in Buffer A (20 mM Tris-HCl, pH 7.5, 400 mM NaCl, 5% glycerol, 1 mM dithiothreitol abbreviated as DTT), a protease inhibitor phenylmethanesulfonyl fluoride (PMSF) with the final concentration of 1 mM is added. Then the cells are lysed using a high-pressure homogenizer and centrifuged a freezing high-speed centrifuge at 18000 rpm for 50 minutes. The supernatant is filtered with a 0.45 micrometers (m) filter membrane. A proper amount of nickel-nitrilotriacetic acid (Ni-NTA) resin is added to a gravity purification column (also referred to as gravity flow column), and Ni beads are activated three times by using Buffer A with 3 times the volume of Ni beads and Buffer A with 10 mM imidazole. The filtered supernatant is added to the gravity purification column containing Ni-NTA resin, and combine at 4° C. for 50 minutes in a chromatography cabinet using a silent mixer. The protein is washed with Buffer A containing 20 mM and 50 mM imidazole respectively, and then eluted with Buffer A containing 75 mM, 100 mM, 200 mM, 300 mM, 400 mM and 500 mM imidazole. Each washing volume is 3-5 times the volume of Ni beads.

A total of 40 microliters (L) of supernatant of broken bacteria, flow-through, eluents with different imidazole gradients are taken and put in a 1.5 mL centrifuge tube, 10 μL 5× protein loading buffer is added, and the protein is denatured after reaction at 100° C. for 10 minutes. 10% sodium dodecyl sulfate-polyacrylamide gel electrophoresis (SDS-PAGE) protein gel is prepared, and the results of affinity purification of protein using Ni beads are analyzed by SDS-PAGE. The eluted target protein with high purity is selected and performed with ultrafiltration concentration by using a 50 kilodaltons (kDa) Amicon® ultrafiltration tube. The concentrated proteins are packaged and stored, quickly frozen with liquid nitrogen and stored in a refrigerator at −80° C.

Figure 1:
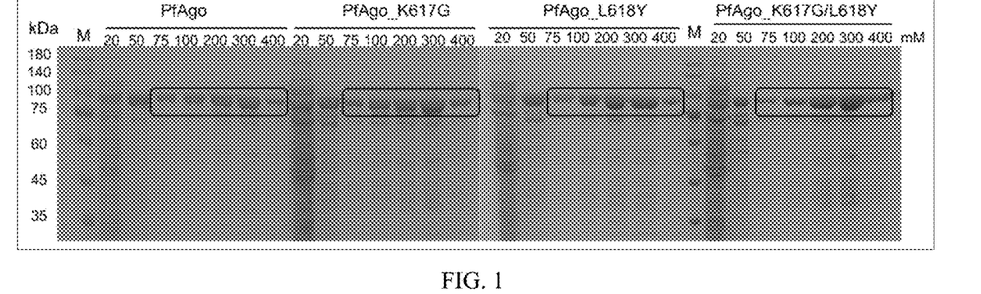
FIG. 1 illustrates a diagram showing analysis results of a *Pyrococcus furiosus* Argonaute (PfAgo) protein and some mutant proteins detected by sodium dodecyl sulfate-polyacrylamide gel electrophoresis (SDS-PAGE) according to an embodiment 1 of the disclosure.

The results of SDS-PAGE identification and analysis of PfAgo and some of its mutants are shown in FIG. 1. It can be seen from FIG. 1 that 20-50 mM imidazole can remove most of the impure proteins, and the purity of the target proteins eluted at 75-400 mM is equivalent.

Finally, the target proteins eluted by 75 mM-400 mM imidazole are selected for ultrafiltration concentration.

After affinity purification of Ni beads, it is necessary to determine the absorbance at 260/280 nm ($A_{260}/A_{280}$, detected for nucleic acid concentration) value of PfAgo and its mutant proteins to determine the amount of endogenous nucleic acid bound in the expression of *Escherichia coli*. After determination, the $A_{260}/A_{280}$ values of PfAgo and its mutant proteins purified by Ni bead affinity are all around 0.65, which can be used in subsequent experiments without further purification.

Embodiment 2 Determination of Cleavage Activity of PfAgo Mutants at Medium Temperature The activity of the selected PfAgo mutants is verified at 37° C. Four types of single-stranded guide nucleic acids, including 5'-hydroxylated guide DNA(5'OH-gDNA), 5'-phosphorylated guide DNA (5'P-gDNA), 5'-hydroxylated guide RNA (5'OH-gRNA) and 5'-phosphorylated guide RNA (5'P-gRNA), are used to cleave the target DNA and the target RNA. Among them, the sequences of the guides and targets used in this embodiment are shown in Table 1.

TABLE 1

| Name | Sequence (5'-3') |
| --- | --- |
| FAM-T-tDNA | FAM-AAACGACGGCCAGTGCCAAGCTTACTATACAAC CTACTACCTCAT (SEQ ID NO: 4) |
| FAM-T-tRNA | FAM-AAACGACGGCCAGUGCCAAGCUUACUAUACAAC CUACUACCUCAU (SEQ ID NO: 5) |
| T-gDNA | TGAGGTAGTAGGTTGTAT (SEQ ID NO: 6) |
| U-gRNA | UGAGGUAGUAGGUUGUAU (SEQ ID NO: 7) |

The enzyme-free PCR tube is added with the guide nucleic acid with the final concentration of 1 μM, PfAgo mutant protein with the final concentration of 1 μM, 1× reaction buffer (10 mM 4-(2-Hydroxyethyl)piperazine-1-ethane-sulfonic acid also referred to as HEPES, pH 7.5, 100 mM NaCl, 5% glycerol, 5 mM $MnCl_2$) containing 5 mM $MnCl_2$, 0.8 units (U)/10 μL RNAase inhibitor, and incubated at 37° C. for 10 minutes. Then, 200 nanomoles per liter (nM) 5'-FAM labeled target DNA or target RNA is added, and reacted at 37° C. for 30 minutes for target cleavage. The reaction is terminated by mixing the sample with 2×RNA loading dyes (95% formamide, 18 mM ethylenediaminetetraacetic acid abbreviated as EDTA, 0.025% SDS and 0.025% bromophenol blue) and heated at 95° C. for 5 minutes. The cleavage products are detected by 20% denatured polyacrylamide gel electrophoresis, and the results are observed by gel imaging system.

Figure 2:
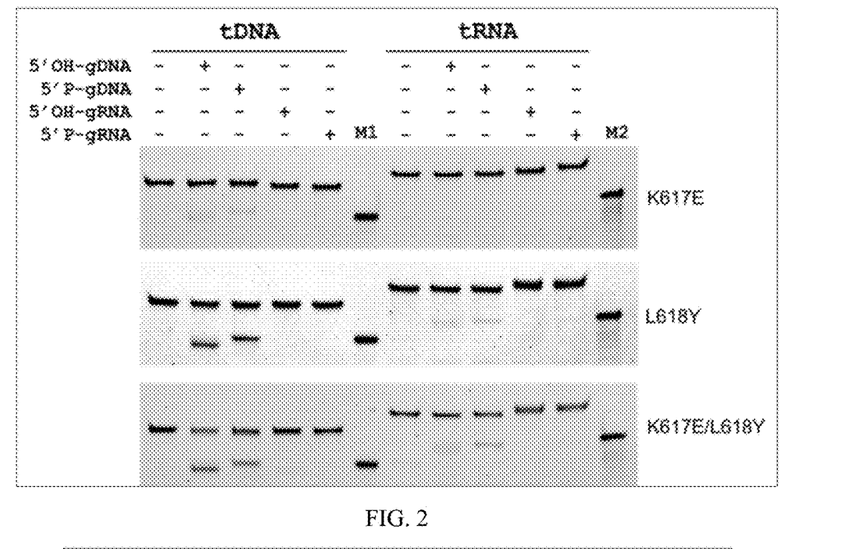
FIG. 2 illustrates a diagram showing results of products obtained by cleaving a single-stranded target DNA or a single-stranded target RNA by PfAgo_K617E, PfAgo_L618Y, and PfAgo_K617E/L618Y detected by urea/polyacrylamide gel electrophoresis according to an embodiment 2 of the disclosure.

The cleavage results of single-stranded target DNA and target RNA by PfAgo_K617E, PfAgo_L618Y and PfAgo_K617E/L618Y are shown in FIG. 2. It can be seen from FIG. 2 that both PfAgo_K617E and PfAgo_L618Y can cleave complementary target DNA under the guidance of 5'OH-gDNA and 5'P-gDNA, but the cleavage activity of PfAgo_K617E is weaker than that of PfAgo_L618Y. Moreover, PfAgo_L618Y can also cleave complementary target RNA under the guidance of 5'OH-gDNA and 5'P-gDNA. PfAgo_K617E/L618Y obtained by combined mutation of these two sites further improves its activity at medium temperature. PfAgo_K617E/L618Y can cleave target DNA and target RNA under the guidance of 5'OH-gDNA and 5'P-gDNA at 37° C., and has a preference for target DNA.

Figure 3:
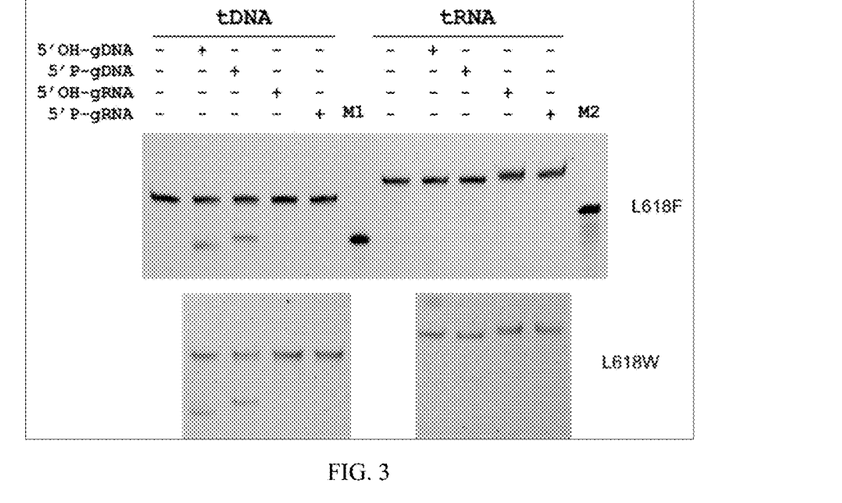
FIG. 3 illustrates a diagram showing results of products obtained by cleaving the single-stranded target DNA or the single-stranded target RNA by PfAgo_L618F and PfAgo_L618W detected by the urea/polyacrylamide gel electrophoresis according to the embodiment 2 of the disclosure.

The cleavage results of PfAgo_L618F and PfAgo_L618W on single-stranded target DNA and target RNA are shown in FIG. 3. It can be seen from FIG. 3 that both PfAgo_L618F and PfAgo_L618W can cleave complementary target DNA under the guidance of 5'OH-gDNA and 5'P-gDNA at 37° C., but they cannot cleave target RNA.

Figure 4:
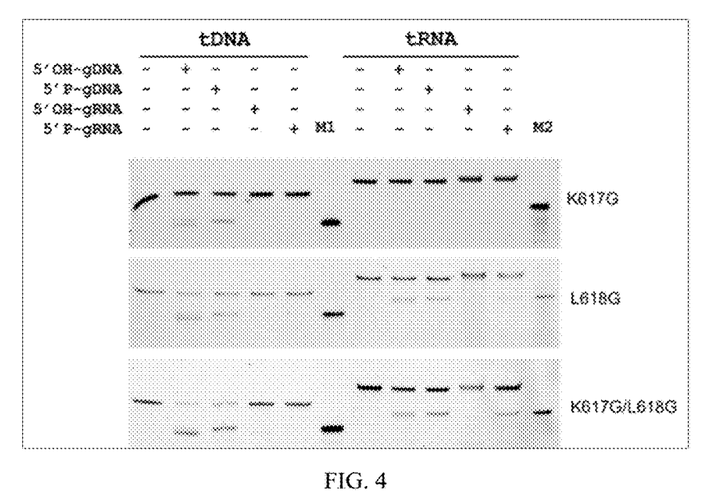
FIG. 4 illustrates a diagram showing results of products obtained by cleaving the single-stranded target DNA or the single-stranded target RNA by PfAgo_K617G, PfAgo_L618G and PfAgo_K617G/L618G detected by the urea/polyacrylamide gel electrophoresis according to the embodiment 2 of the disclosure.

The cleavage results of single-stranded target DNA and target RNA by PfAgo_K617G, PfAgo_L618G and PfAgo_K617G/L618G are shown in FIG. 4. It can be seen from FIG. 4 that PfAgo_K617G can cleave complementary target DNA with 5'OH-gDNA and 5'P-gDNA, and its activity is stronger than that of PfAgo_K617E. PfAgo_L618G can cleave complementary target DNA and target RNA with 5'OH-gDNA and 5'P-gDNA, and its activity is stronger than that of PfAgo_L618Y. Moreover, PfAgo_L618Y can cleave complementary target RNA with 5'P-gRNA, even though its activity is weak. PfAgo_K617G/L618G obtained by combined mutation of two sites further improves its activity at medium temperature. PfAgo_K617G/L618G can cleave complementary target DNA at 37° C. using 5'OH-gDNA and 5'P-gDNA, and can cleave complementary target RNA using 5'OH-gDNA, 5'P-gDNA, and 5'P-gRNA.

Embodiment 3 Determination of Cleavage Activity of PfAgo Mutants at High Temperature Referring to the embodiment 2, in this embodiment, mutants PfAgo_K617E, PfAgo_L618Y and PfAgo_K617E/L618Y are used to carry out 5'P-gDNA-guided target DNA cleavage experiments at 37° C. and 95° C., respectively (PfAgo is used as control).

Figure 5:
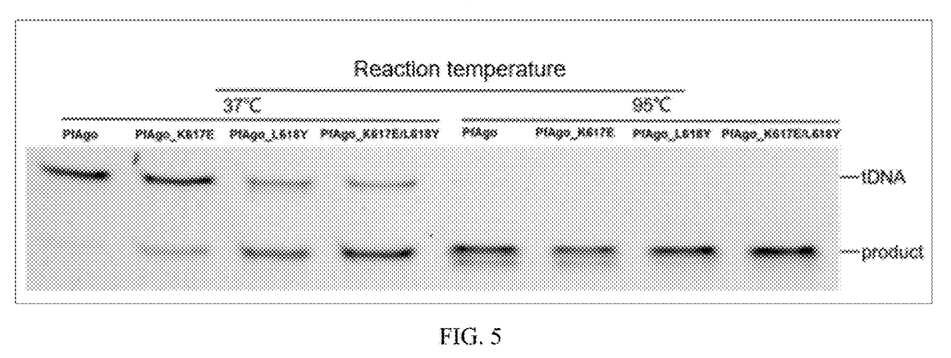
FIG. 5 illustrates a diagram showing results of products obtained by cleaving the target DNA by the PfAgo and its mutants PfAgo_K617E, PfAgo_L618Y and PfAgo_K617E/L618Y under the guidance of 5'-phosphorylated guide DNA (5'P-gDNA) detected by the urea/polyacrylamide gel electrophoresis according to an embodiment 3 of the disclosure.

The cleavage results of single-stranded target DNA by PfAgo_K617E, PfAgo_L618Y and PfAgo_K617E/L618Y are shown in FIG. 5. It can be seen from FIG. 5 that PfAgo_K617E, PfAgo_L618Y and PfAgo_K617E/L618Y can not only cleave targets at 37° C., but also maintain high activity at 95° C.

Embodiment 4 Effect of Length of Guide Nucleic Acid on Cleavage Activity of PfAgo_K617G/L618G In this embodiment, the mutant PfAgo_K617G/L618G is taken as an example to explore the optimal length of the guide nucleic acid.

According to the guide nucleic acid sequence and the target sequence in the embodiment 2, gDNA and gRNA with the length of 12-30 nucleotides (nt) are synthesized. Specifically, the sequence of 30 nt gDNA is shown in Table 2, and the sequence of 12-25 nt gDNA is consistent with the first 12, 13, 14, 15, 16, 17, 18, 19, 20, 21 and 25 bases of this sequence respectively. The sequence of 30 nt gRNA is shown in Table 2, and the sequence of 12-25 nt gRNA is consistent with the first 12, 13, 14, 15, 16, 17, 18, 19, 20, 21 and 25 bases of this sequence respectively. These guide nucleic acids have the same sequence at the 5' end, so that the size of cleavage sites and cleavage products should be identical. The synthesized guide nucleic acids of different lengths are phosphorylated at the 5' end, the cleavage experiments of target DNA and target RNA are carried out with 5'P-gDNA with different lengths, and the cleavage experiments of target RNA are carried out with 5'P-gRNA with different lengths. The experimental process is as follows in the embodiment 2.

TABLE 2

| Name | Sequence (5'-3') |
| --- | --- |
| 30nt gDNA | TGAGGTAGTAGGTTGTATAGTAAGCTTGGC (SEQ ID NO: 8) |
| 30nt gRNA | UGAGGUAGUAGGUUGUAUAGUAAGCUUGGC (SEQ ID NO: 9) |

Figure 6:
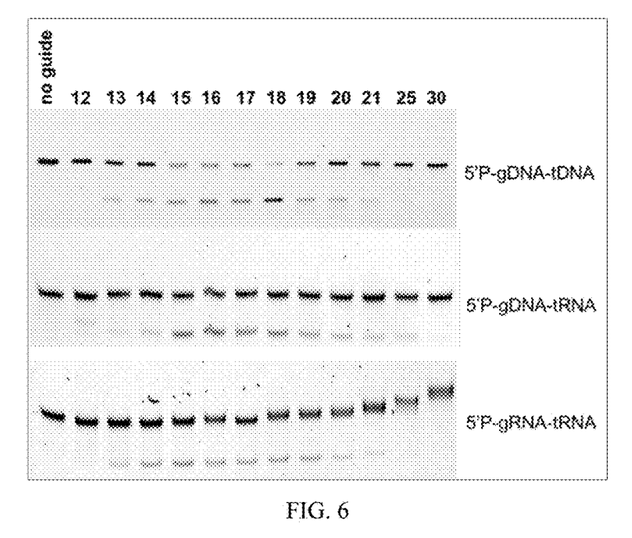
FIG. 6 illustrates a diagram showing results of products obtained by cleaving the single-stranded target DNA or the single-stranded target RNA by the PfAgo_K617G/L618G with different lengths of guide nucleic acid detected by the urea/polyacrylamide gel electrophoresis according to an embodiment 4 of the disclosure.

20% urea/polyacrylamide gel electrophoresis is used for detection, and the detection result is shown in FIG. 6. The results show that PfAgo_K617G/L618G could use 5'P-gDNA with the length of 13-25 nt to cleave the target DNA, and show the highest enzyme cleavage activity under the guidance of 18 nt guide nucleic acid. PfAgo_K617G/L618G can cleave the target RNA under the guidance of 5'P-gDNA with the length of 12-30 nt, and it shows high enzyme cleavage activity under the guidance of 15-18 nt guide nucleic acid. PfAgo_K617G/L618G can cleave the target RNA under the guidance of 5'P-gRNA with the length of 13-21 nt, and it shows high enzyme cleavage activity under the guidance of 14-19 nt guide nucleic acid.

Embodiment 5 Effect of Different Bivalent Metal Ions on the Cleavage Activity of PfAgo_K617G/L618G In this embodiment, the mutant PfAgo_K617G/L618G is taken as an example to explore the effect of divalent metal ions in the cleavage system on the cleavage activity of the mutant.

The experimental process refers to the embodiment 2, but unlike the embodiment 2, $MnCl_2$ in the enzyme cleavage reaction buffer is replaced with the same concentration of $FeCl_2$, $CoCl_2$, $NiCl_2$, $CuCl_2$, $ZnCl_2$, $CaCl_2$, $MgCl_2$ and EDTA to carry out 5'P-gDNA-guided tDNA, tRNA and 5'P-gRNA-guided tRNA cleavage experiments.

Figure 7:
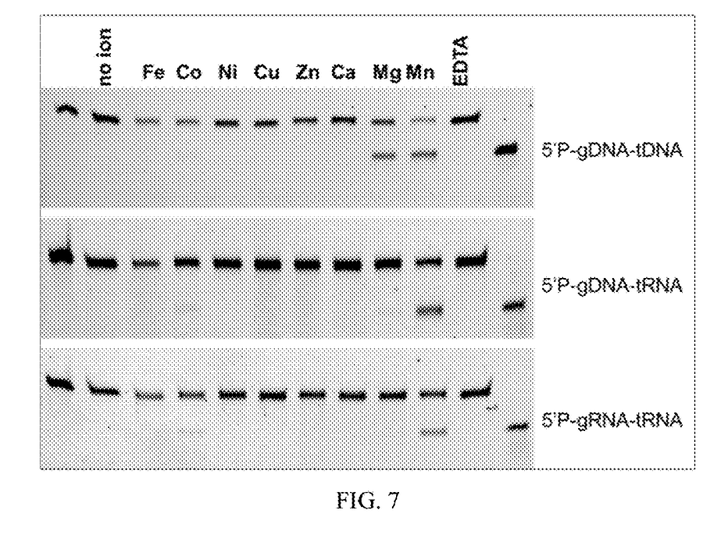
FIG. 7 illustrates a diagram showing results of products obtained by cleaving the single-stranded target DNA or the single-stranded target RNA by the PfAgo_K617G/L618G under different metal cations detected by the urea/polyacrylamide gel electrophoresis according to an embodiment 5 of the disclosure.

20% urea/polyacrylamide gel electrophoresis is used for detection, and the detection results are shown in FIG. 7. The results show that PfAgo_K617G/L618G can use $Co^{2+}$, $Mg^{2+}$ and $Mn^{2+}$ as divalent metal ions for 5'P-gDNA-guided cleavage of target DNA, and it has the best activity in the enzyme cleavage buffer containing $Mn^{2+}$. For the cleavage of target RNA guided by 5'P-gDNA, PfAgo_K617G/L618G can also use $Co^{2+}$, $Mg^{2+}$ and $Mn^{2+}$ as divalent metal ions, and it has the best activity in the enzyme cleavage buffer containing $Mn^{2+}$. For the cleavage of target RNA guided by 5'P-gRNA, PfAgo_K617G/L618G can only use $Co^{2+}$ and $Mn^{2+}$ as divalent metal ions, and it has the best activity in the enzyme cleavage buffer containing $Mn^{2+}$. Thus, the optimal divalent metal ion of PfAgo_K617G/L618G is $Mn^{2+}$.

In this embodiment, the effects of different concentrations of $Mn^{2+}$ and $Mg^{2+}$ on the cleavage activity of PfAgo_K617G/L618G are further investigated. The cleavage activity of PfAgo_K617G/L618G is tested at different concentrations of $Mn^{2+}$ and $Mg^{2+}$ (1, 2, 3, 4, 5, 10 mM).

Figure 8:
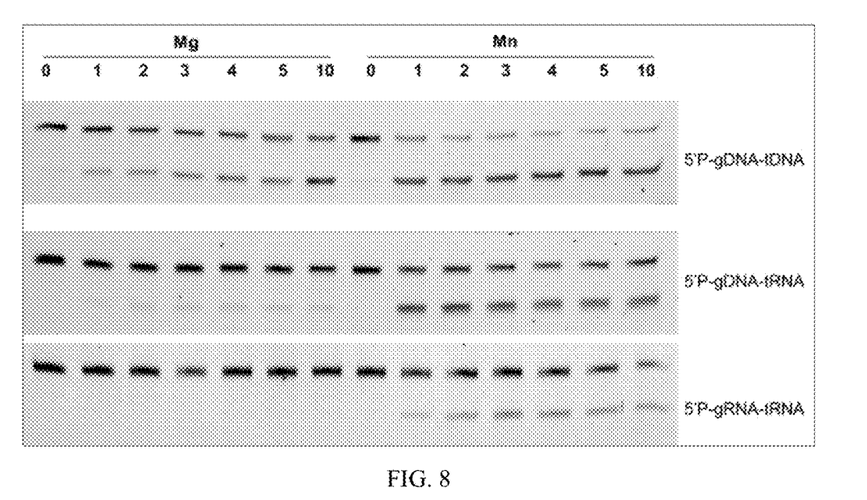
FIG. 8 illustrates a diagram showing results of products obtained by cleaving the single-stranded target DNA or the single-stranded target RNA by the PfAgo_K617G/L618G under different $Mn^{2+}$ or $Mg^{2+}$ ion concentrations detected by the urea/polyacrylamide gel electrophoresis according to the embodiment 5 of the disclosure.

20% urea/polyacrylamide gel electrophoresis is used for detection, and the detection result is shown in FIG. 8. The results show that when 5'P-gDNA is used for targeted cleavage of complementary single-stranded DNA, the $Mg^{2+}$ titration experiment shows that PfAgo_K617G/L618G had catalytic activity at the ion concentration of 1-10 mM, and the activity is the strongest at the ion concentration of 10 mM. $Mn^{2+}$ titration experiment shows that PfAgo_K617G/L618G has catalytic activity at the ion concentration of 1-10 mM, and the activity is strong and comparable at the ion concentration of 2-10 mM. When 5'P-gDNA is used for targeted cleavage of complementary RNA, the $Mg^{2+}$ titration experiment shows that PfAgo_K617G/L618G has catalytic activity at the ion concentration of 1-10 mM, and the activity is comparable but generally weak at the ion concentration of 2-10 mM. $Mn^{2+}$ titration experiment shows that PfAgo_K617G/L618G has catalytic activity at the ion concentration of 1-10 mM, and the cleavage activity is comparable. When 5'P-gRNA is used for targeted cleavage of complementary RNA, the $Mg^{2+}$ titration experiment shows that PfAgo_K617G/L618G cannot perform targeted cleavage even if the $Mg^{2+}$ ion concentration is increased to 10 mM. $Mn^{2+}$ titration experiment shows that PfAgo_K617G/L618G has catalytic activity at the ion concentration of 1-10 mM, and the activity is strong and comparable at the ion concentration of 3-10 mM.

Embodiment 6 Effect of 5'-Terminal Nucleotide of Guide Nucleic Acid on Enzyme Cleavage Activity of PfAgo_K617G/L618G In this embodiment, the mutant PfAgo_K617G/L618G is taken as an example to explore the effect of 5'-terminal nucleotide of guide nucleic acid on enzyme cleavage activity.

Referring to the guide nucleic acid sequence in the embodiment 2, a series of 5'-terminal phosphorylated DNA and RNA guide nucleic acids are designed and synthesized, with different 5'-terminal nucleotides (A, T/U, G, C) but identical sequences in other parts. Correspondingly, a series of target DNA and RNA complementary to various guide nucleic acids are also synthesized, and the sequences of the corresponding targets are shown in Table 3.

TABLE 3

| Name | Sequence (5'-3') |
| --- | --- |
| FAM-A-tDNA | FAM-AAACGACGGCCAGTGCCAAGCTTACTATACAA CCTACTACCTCTT (SEQ ID NO: 10) |
| FAM-T-tDNA | FAM-AAACGACGGCCAGTGCCAAGCTTACTATACAA CCTACTACCTCAT (SEQ ID NO: 4) |
| FAM-G-tDNA | FAM-AAACGACGGCCAGTGCCAAGCTTACTATACAA CCTACTACCTCCT (SEQ ID NO: 11) |
| FAM-C-tDNA | FAM-AAACGACGGCCAGTGCCAAGCTTACTATACAA CCTACTACCTCGT (SEQ ID NO: 12) |
| FAM-A-tRNA | FAM-AAACGACGGCCAGUGCCAAGCUUACUAUACAA CCUACUACCUCUU (SEQ ID NO: 13) |
| FAM-T-tRNA | FAM-AAACGACGGCCAGUGCCAAGCUUACUAUACAA CCUACUACCUCAU (SEQ ID NO: 5) |
| FAM-G-tRNA | FAM-AAACGACGGCCAGUGCCAAGCUUACUAUACAA CCUACUACCUCCU (SEQ ID NO: 14) |
| FAM-C-tRNA | FAM-AAACGACGGCCAGUGCCAAGCUUACUAUACAA CCUACUACCUCGU (SEQ ID NO: 15) |

Figure 9:
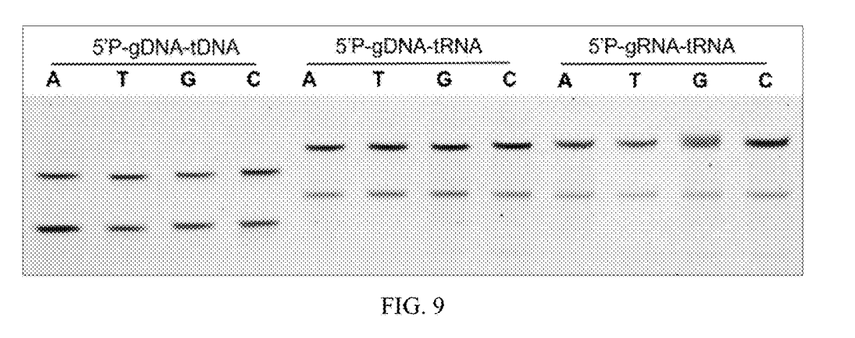
FIG. 9 illustrates a diagram showing results of products obtained by cleaving the single-stranded target DNA or the single-stranded target RNA by the PfAgo_K617G/L618G under the guidance of guide nucleic acids with different 5'-terminal nucleotides detected by the urea/polyacrylamide gel electrophoresis according to an embodiment 6 of the disclosure.

The activity of cleaving single-stranded DNA and RNA is tested under the guidance of 5'P-gDNA with different 5'-terminal nucleotides, and the activity of cleaving RNA is tested under the guidance of 5'P-gRNA with different 5'-terminal nucleotides (the testing process is the same as in the embodiment 2), and 20% urea/polyacrylamide gel electrophoresis is used for detection. The detection results are shown in FIG. 9.

The results show that when PfAgo_K617G/L618G cleaves complementary single-stranded target DNA under the guidance of 5'P-gDNA, the cleavage activity mediated by the guide nucleic acid containing 5'-A is slightly higher than that of the guide nucleic acids containing 5'-T, 5'-G and 5'-C, and the guide nucleic acids containing 5'-T, 5'-G and 5'-C are comparable. When PfAgo_K617G/L618G cleaves complementary target RNA under the guidance of 5'P-gDNA and 5'P-gRNA, no obvious preference for 5'-terminal nucleotides is observed, and the cleavage activities mediated by the guide nucleic acids containing 5'-A, 5'-T/U, 5'-G and 5'-C are comparable.

Embodiment 7 Kinetics Analysis of Target Cleavage of PfAgo_K617G/L618G

In this embodiment, the kinetics of target cleavage of PfAgo_K617G/L618G is studied. The experimental conditions and process refer to the embodiment 2, and 5'P-gDNA-guided tDNA, tRNA and 5'P-gRNA-guided tRNA cleavage experiments are carried out at 37° C. for different time (0, 5, 10, 15, 30, 45, 60 minutes). The cleavage products are detected by 20% denatured polyacrylamide gel electrophoresis, and the results are observed by gel imaging system.

and synthesized with reference to the guide nucleic acid sequence and target sequence in the embodiment 2, and a single base mismatch would occur between these guide nucleic acids and target DNA or target RNA. The sequences of guide nucleic acids with single base mismatch at different sites are shown in Table 4.

TABLE 4

| Name | Mismatch site information | Name | Mismatch site information |
|---|---|---|---|
| gDNA_mm1 | Mismatch at 1$^{st}$ site of T-gDNA is A | gRNA_mm1 | Mismatch at 1$^{st}$ site of U-gRNA is A |
| gDNA_mm2 | Mismatch at 2$^{nd}$ site of T-gDNA is C | gRNA_mm2 | Mismatch at 2$^{nd}$ site of U-gRNA is C |
| gDNA_mm3 | Mismatch at 3$^{rd}$ site of T-gDNA is T | gRNA_mm3 | Mismatch at 3$^{rd}$ site of U-gRNA is U |
| gDNA_mm4 | Mismatch at 4$^{th}$ site of T-gDNA is C | gRNA_mm4 | Mismatch at 4$^{th}$ site of U-gRNA is C |
| gDNA_mm5 | Mismatch at 5$^{th}$ site of T-gDNA is C | gRNA_mm5 | Mismatch at 5$^{th}$ site of U-gRNA is C |
| gDNA_mm6 | Mismatch at 6$^{th}$ site of T-gDNA is A | gRNA_mm6 | Mismatch at 6$^{th}$ site of U-gRNA is A |
| gDNA_mm7 | Mismatch at 7$^{th}$ site of T-gDNA is T | gRNA_mm7 | Mismatch at 7$^{th}$ site of U-gRNA is U |
| gDNA_mm8 | Mismatch at 8$^{th}$ site of T-gDNA is C | gRNA_mm8 | Mismatch at 8$^{th}$ site of U-gRNA is C |
| gDNA_mm9 | Mismatch at 9$^{th}$ site of T-gDNA is A | gRNA_mm9 | Mismatch at 9$^{th}$ site of U-gRNA is A |
| gDNA_mm10 | Mismatch at 10$^{th}$ site of T-gDNA is T | gRNA_mm10 | Mismatch at 10$^{th}$ site of U-gRNA is U |
| gDNA_mm11 | Mismatch at 11$^{th}$ site of T-gDNA is C | gRNA_mm11 | Mismatch at 11$^{th}$ site of U-gRNA is C |
| gDNA_mm12 | Mismatch at 12$^{th}$ site of T-gDNA is C | gRNA_mm12 | Mismatch at 12$^{th}$ site of U-gRNA is C |
| gDNA_mm13 | Mismatch at 13$^{th}$ site of T-gDNA is A | gRNA_mm13 | Mismatch at 13$^{th}$ site of U-gRNA is A |
| gDNA_mm14 | Mismatch at 14$^{th}$ site of T-gDNA is A | gRNA_mm14 | Mismatch at 14$^{th}$ site of U-gRNA is A |
| gDNA_mm15 | Mismatch at 15$^{th}$ site of T-gDNA is C | gRNA_mm15 | Mismatch at 15$^{th}$ site of U-gRNA is C |
| gDNA_mm16 | Mismatch at 16$^{th}$ site of T-gDNA is A | gRNA_mm16 | Mismatch at 16$^{th}$ site of U-gRNA is A |
| gDNA_mm17 | Mismatch at 17$^{th}$ site of T-gDNA is T | gRNA_mm17 | Mismatch at 17$^{th}$ site of U-gRNA is U |
| gDNA_mm18 | Mismatch at 18$^{th}$ site of T-gDNA is A | gRNA_mm18 | Mismatch at 18$^{th}$ site of U-gRNA is A |

The above experiment is repeated three times. The polyacrylamide gel electrophoresis (PAGE) gels of nucleic acid denaturation are scanned by ImageJ software, the cleavage ratio of PfAgo is calculated by Microsoft Excel software, and the data is plotted by Prism8 (GraphPad) software for statistical analysis. The data are expressed as the average±standard deviation (SD) of three independent experiments.

Figure 10:
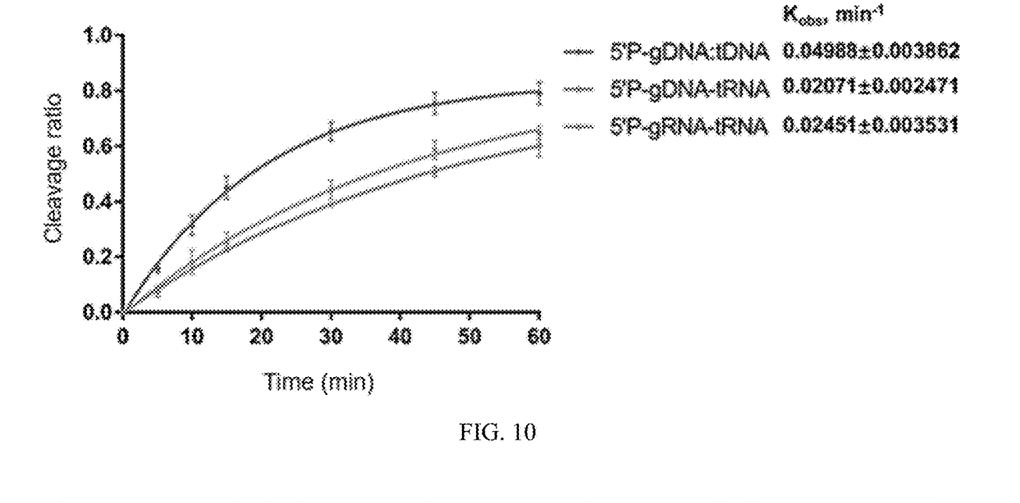
FIG. 10 illustrates a diagram showing analysis results of target cleavage kinetics of the PfAgo_K617G/L618G according to an embodiment 7 of the disclosure.

The analysis results are shown in FIG. 10. The results show that the cleavage of target DNA guided by 5'P-gDNA has the fastest reaction rate, with a $k_{obs}$ value of 0.04988±0.003862, followed by the cleavage of target RNA guided by 5'P-gDNA and 5'P-gRNA, with $k_{obs}$ values of 0.02071±0.002471 and 0.02451±0.003531 respectively.

Embodiment 8 Effect of Single Base Mismatch of Guide/Target on Enzyme Cleavage Activity of PfAgo_K617G/L618G In this embodiment, the mutant PfAgo_K617G/L618G is taken as an example to study the effect of single base mismatch at different sites on the enzyme cleavage activity of the mutant.

Firstly, a series of gDNA and gRNA with single bases different from the original guide nucleic acid are designed Then, these guide nucleic acids are phosphorylated at the 5' end, and the target DNA and the target RNA are cleaved with 5'P-gDNA and the target RNA is cleaved with 5'P-gRNA with reference to the embodiment 2, and the cleavage products are detected by 20% urea/polyacrylamide gel electrophoresis.

Figure 11:
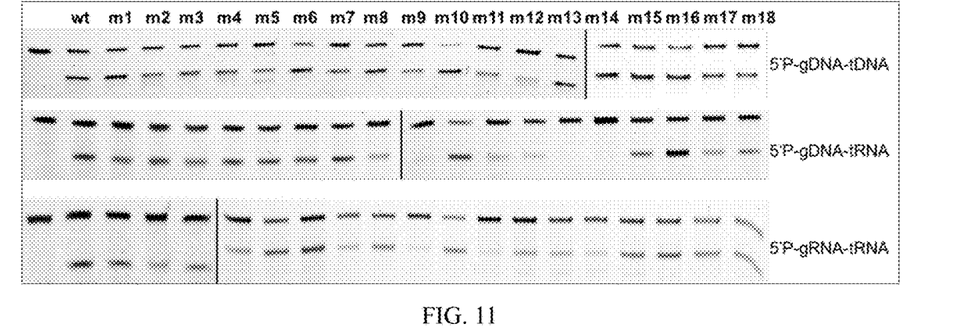
FIG. 11 illustrates a diagram showing results of products obtained by cleaving the single-stranded target DNA or the single-stranded target RNA by the PfAgo_K617G/L618G under different single base mismatch conditions detected by the urea/polyacrylamide gel electrophoresis according to an embodiment 8 of the disclosure.

The detection results are shown in FIG. 11. The results show that when the target DNA is cleaved under the guidance of 5'P-gDNA, the single base mismatches occurring at the 2$^{nd}$, 3$^{rd}$, 4$^{th}$, 5$^{th}$ and 7$^{th}$ sites in the seed region and the 9$^{th}$, 11$^{th}$ and 12$^{th}$ sites in the central region of the guide nucleic acid will reduce the enzyme cleavage activity of PfAgo_K617G/L618G, especially the single base mismatch at the 12$^{th}$ site in the central region of the guide nucleic acid will greatly reduce its enzyme cleavage activity. On the contrary, the single base mismatch in the 5' anchor region, 3' complement region and 3' tail region of the guide nucleic acid do not significantly reduce the cleavage activity, but the mismatch in some sites also improve its cleavage activity. When the target RNA is cleaved under the guidance of 5'P-gDNA, the single-base mismatches occurring at 8$^{th}$ sites in the seed region, 9$^{th}$, 11$^{th}$, and 12$^{th}$ sites in the central region, and 13$^{th}$ and 14$^{th}$ sites in the 3' complement region will reduce the enzyme cleavage activity of PfAgo_K617G/L618G, especially at 13$^{th}$ and 14$^{th}$ sites in the 3' complement region of the guide nucleic acid will lose enzyme activity. On the contrary, the single base mismatch in the 5' anchor region and 3' tail region of the guide nucleic acid does not significantly reduce its cleavage activity, and the single base mismatch in the $10^{th}$ site of the central region of the guide nucleic acid also improves the enzyme cleavage activity. When the target RNA is cleaved under the guidance of 5'P-gRNA, the single base mismatches occurring at $2^{nd}$, $3^{rd}$, $4^{th}$ and $7^{th}$ sites in the seed region, $9^{th}$, $11^{th}$ and $12^{th}$ sites in the central region, and $13^{th}$ and $14^{th}$ sites in the 3' complement region will reduce the enzyme cleavage activity of PfAgo_K617G/L618G, especially at $9^{th}$ and $11^{th}$ sites in the central region of the guide nucleic acid will greatly reduce its enzyme cleavage activity. On the contrary, the single base mismatches in the 5' anchor region and 3' tail region of the guide nucleic acid do not significantly reduce its cleavage activity, and the single base mismatch at the $10^{th}$ site in the central region of the guide nucleic acid also improves the enzyme cleavage activity.

Embodiment 9 Detection of Plasmid Cleavage by PfAgo_K617G/L618G

In this embodiment, the mutant PfAgo_K617G/L618G is taken as an example to detect the cleavage activity of the mutant on plasmid DNA.

The guide DNA targeting different GC content regions of plasmid is first synthesized, diluted to 100 μM with nuclease-free water, subjected to 5' phosphorylation treatment and stored separately for later use. The sequence of guide DNA targeting different GC content regions is shown in Table 5.

TABLE 5

| Name | Sequence (5'-3') |
|---|---|
| 26gD-F | CATGAGCGGATACATATT (SEQ ID NO: 16) |
| 26gD-R | CAAATATGTATCCGCTCA (SEQ ID NO: 17) |
| 29gD-F | TCAAAAAGGATCTTCACC (SEQ ID NO: 18) |
| 29gD-R | TAGGTGAAGATCCTTTTT (SEQ ID NO: 19) |
| 39gD-F | AAGAAACCATTATTATCA (SEQ ID NO: 20) |
| 39gD-R | CATGATAATAATGGTTTC (SEQ ID NO: 21) |
| 45gD-F | AAAAGTGCTCATCATTGG (SEQ ID NO: 22) |
| 45gD-R | TTCCAATGATGAGCACTT (SEQ ID NO: 23) |
| 53gD-F | CAGGGTTTTCCCAGTCAC (SEQ ID NO: 24) |
| 53gD-R | TCGTGACTGGGAAAACCC (SEQ ID NO: 25) |

1 μM PfAgo mutant and 1 μM forward or reverse guide nucleic acid are premixed in reaction buffer containing 5 mM HEPES pH 7.5, 50 mM NaCl, 2 mM MnCl$_2$ and 2.5% glycerol, respectively, and reacted at 60° C. for 30 minutes to bind the guide nucleic acid. Then, two different reaction solutions are mixed, and then 200 nanograms (ng) of target plasmid pUC19 are added, and the target is cleaved at 37° C. for 1 hour. Linear double-stranded DNA is cleaved by digestion with NdeI or ScaI restriction endonuclease in Cutsmart buffer at 37° C. for 1 hour. The cleavage products are mixed with 6×DNA loading buffer, detected by 1% agarose gel electrophoresis, stained by Ethidium bromide (EB), and observed by gel imaging system.

Figure 12:
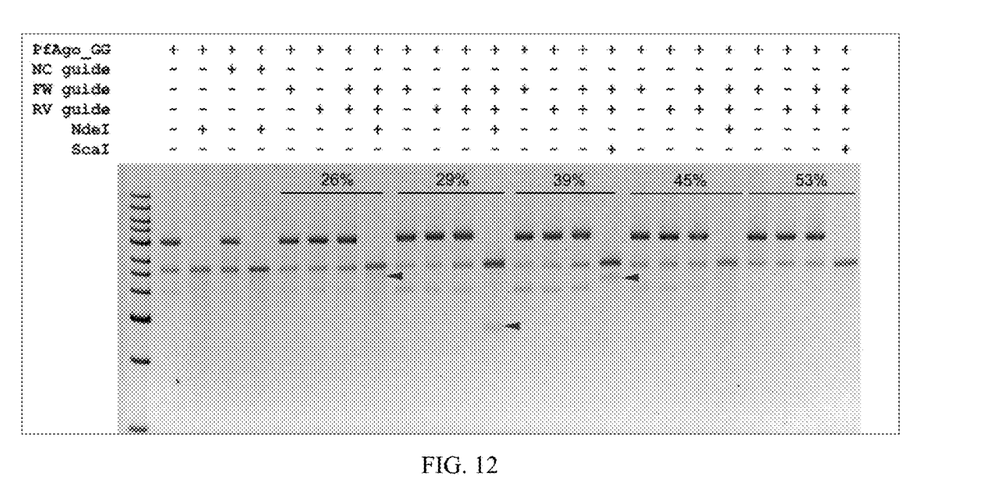
FIG. 12 illustrates a diagram showing detection results of products obtained by cleaving plasmid DNA with the PfAgo_K617G/L618G according to an embodiment 9 of the disclosure.

The detection results are shown in FIG. 12. The results show that as long as PfAgo_K617G/L618G protein is added, the plasmids are mostly of open-loop (OC) and a small amount of linear (Lin) state. However, when adding a pair of 5'P-gDNA corresponding to 26% GC, 29% GC and 39% GC content of the target region, more linear products are detected compared to the addition of one guide nucleic acid. Then, the product is cleaved by restriction endonuclease (NdeI or ScaI), and a product band of an expected size is detected, indicating that PfAgo_K617G/L618G could specifically cleave plasmid DNA at 37° C. When the GC content is 45% and 53%, the expected product band is not observed, indicating that the cleavage efficiency of PfAgo_K617G/L618G plasmid is affected by the target GC content.

Embodiment 10 Study on Heat Resistance of PfAgo_K617G/L618G

In this embodiment, in order to explore the thermal stability of PfAgo_K617G/L618G, the enzyme is pre-bound with the guide nucleic acid at different temperatures, and then its cleavage activity is detected at 37° C. (refer to the embodiment 2 for the experimental process).

Figure 13:
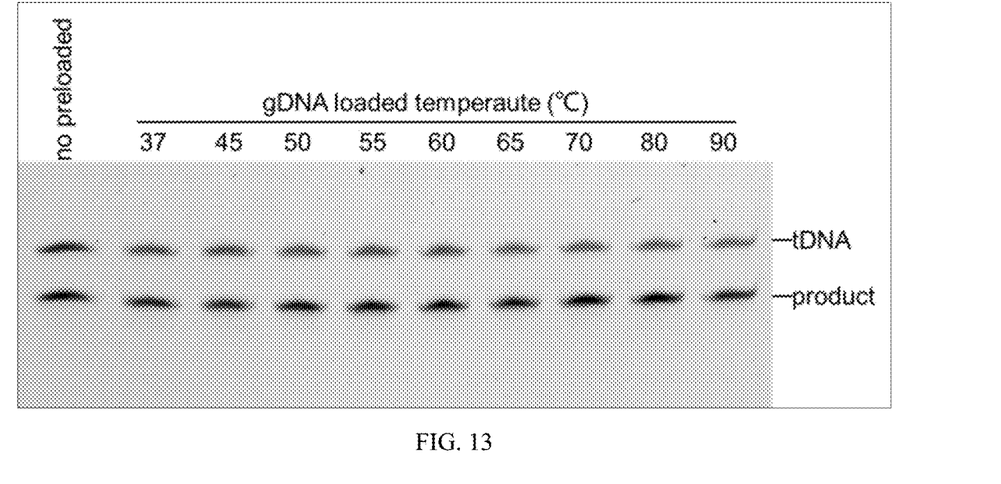
FIG. 13 illustrates a diagram showing detection results of products obtained by cleaving of the target DNA by the PfAgo_K617G/L618G at different guide nucleic acid incubation temperatures according to an embodiment 10 of the disclosure.

The results (FIG. 13) show that PfAgo_K617G/L618G still has good activity at 37° C. even if the incubation temperature is raised to 90° C.

Embodiment 11 Effect of Temperature on Cleavage Activity of PfAgo_K617G/L618G

In this embodiment, the effect of temperature on the cleavage activity of PfAgo_K617G/L618G is explored, and the cleavage activities of tDNA and tRNA guided by 5'P-gDNA and tRNA guided by 5'P-gRNA are tested at different temperatures. The guide and target nucleic acids and test process used in this experiment refer to the embodiment 2.

Figure 14:
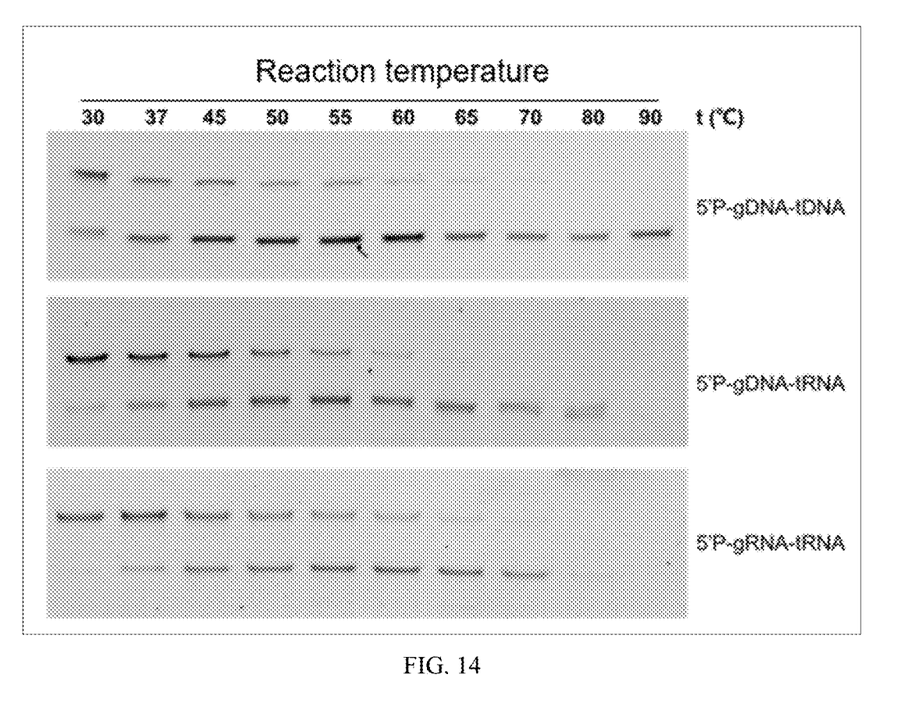
FIG. 14 illustrates a diagram showing detection results of products obtained by cleaving the target DNA or the target RNA at different reaction temperatures by the PfAgo_K617G/L618G according to an embodiment 11 of the disclosure.

The results (FIG. 14) show that the cleavage activity of PfAgo_K617G/L618G is improved with the increase of temperature in the range of 30° C.-90° C.

Embodiment 12 Comparison of Cleavage Rates Between Wild-Type PfAgo and PfAgo_K617G/L618G at High Temperature In this embodiment, the cleavage rates of wild-type PfAgo and PfAgo_K617G/L618G are compared at 95° C. Specifically, the target DNA is cleaved at 95° C. with 5'P-gDNA as the guide. The guide and target nucleic acids and experimental process used in this experiment refer to the embodiment 2, and the cleavage rate analysis refers to the embodiment 7.

Figure 15:
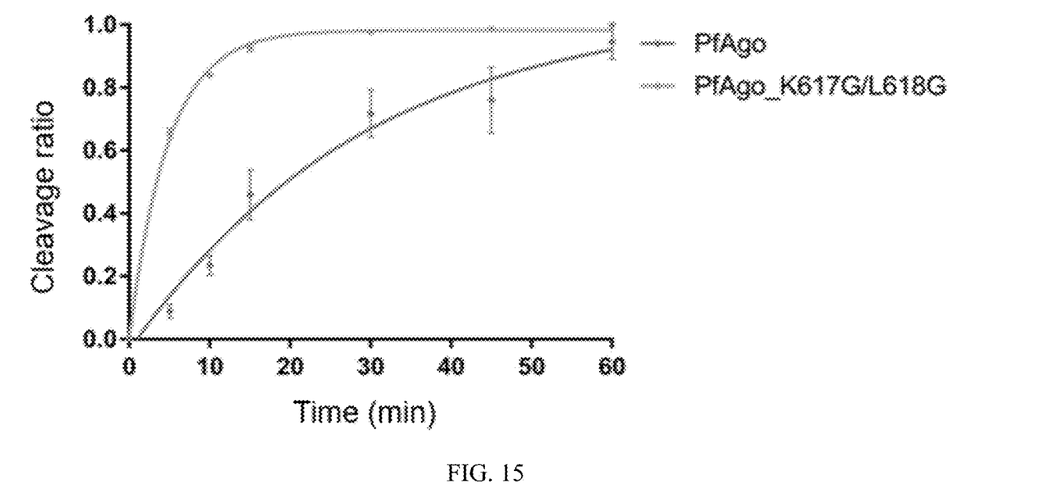
FIG. 15 illustrates a comparison of cleavage ratio of the target DNA by the wild-type PfAgo protein and the PfAgo_K617G/L618G at 95° C. according to an embodiment 12 of the disclosure.

The results (FIG. 15) show that the cleavage rate of PfAgo_K617G/L618G at 95° C. is also faster than that of wild-type PfAgo.

In conclusion, compared with the wild-type PfAgo protein, the PfAgo mutant protein provided by the disclosure not only has better cleavage activity at medium temperature and high temperature, but also has higher cleavage rate, thus effectively expanding the application range of pAgo protein. The disclosure also provides a nucleic acid expression vector for preparing PfAgo mutant protein, and a composition, a kit and a method for cleaving and editing target nucleic acid in a sequence-specific manner, which lays a foundation for the applications of PfAgo mutant protein in many fields of biotechnology, such as nucleic acid detection, molecular cloning, RNA and genome editing.

The above is only some of specific embodiments of the disclosure, and the protection scope of the disclosure is not limited to this. Any change or replacement that can be easily thought of by those skilled in the art within the technical scope disclosed by the disclosure should be included in the protection scope of the disclosure.

What is claimed is:

1. A *Pyrococcus furiosus* Argonaute (PfAgo) mutant protein with mesophilic target nucleic acid cleavage activity, wherein the PfAgo mutant protein has an amino acid mutation on at least one of a $617^{th}$ position and a $618^{th}$ position relative to the sequence shown in SEQ ID NO: 1, making at least one of lysine at the $617^{th}$ position be mutated to another amino acid and leucine at the $618^{th}$ position be mutated to another amino acid.

2. The PfAgo mutant protein as claimed in claim 1, wherein the amino acid mutation of the PfAgo mutant protein is at least one selected from the group consisting of:
   K617E;
   K617G;
   L618Y,
   L618F;
   L618W; and
   L618G.

3. A nucleic acid molecule, encoding the PfAgo mutant protein as claimed in claim 1.

4. An expression cassette, comprising the nucleic acid molecule as claimed in claim 3.

5. A vector, comprising the nucleic acid molecule as claimed in claim 3.

6. A transformant, comprising the nucleic acid molecule as claimed in claim 3.

7. A nucleic acid cleavage system, comprising:
   a single-stranded guide nucleic acid; and
   the PfAgo mutant protein as claimed in claim 1.

8. The nucleic acid cleavage system as claimed in claim 7, wherein a length of the single-stranded guide nucleic acid is in a range of 12-30 nucleotides (nt), and the single-stranded guide nucleic acid is one selected from the group consisting of 5'-phosphorylated guide RNA (5'P-gRNA), 5'-phosphorylated guide DNA (5'P-gDNA), or 5'-hydroxylated guide DNA (5'OH-gDNA).

9. An application method of the nucleic acid cleavage system as claimed in claim 7, comprising:
   specifically cleaving one of a target RNA and a target DNA by using the nucleic acid cleavage system, specifically comprising:
      adding one of the target RNA and the target DNA to the nucleic acid cleavage system, making one of the target RNA and the target DNA be complementary pairing to a sequence of the single-stranded guide nucleic acid, and specifically cleaving one of the target RNA and the target DNA by the PfAgo mutant protein under a guidance of the single-stranded guide nucleic acid; wherein complementary pairing specifically refers to:
      one of the target RNA and the target DNA having a nucleotide sequence that is completely complementary to the sequence of single-stranded guide nucleic acid; or
      one of the target RNA and the target DNA having a nucleotide sequence that has 1, 2, 3, 4, or 5 bases mismatch with the sequence of the single-stranded guide nucleic acid.

10. The application method according to claim 9, wherein the nucleic acid cleavage system comprises at least one selected from the group consisting of manganese ion ($Mn^{2+}$), magnesium ion ($Mg^{2+}$), and cobalt ion ($Co^{2+}$).

11. An application method of the PfAgo mutant protein as claimed in claim 1, comprising:
   performing gene editing using the PfAgo mutant protein.

12. An application method of the nucleic acid cleavage system as claimed in claim 7, comprising:
   performing gene editing using the nucleic acid cleavage system.

13. An application method of the PfAgo mutant protein as claimed in claim 1, comprising:
   preparing a nucleic acid detection kit using the PfAgo mutant protein.

* * * * *